(12) United States Patent
Lang et al.

(10) Patent No.: US 9,050,281 B2
(45) Date of Patent: Jun. 9, 2015

(54) COCCIDIOSIS VACCINES

(75) Inventors: Marcelo Lang, Fairfield, CT (US);
Charles Timothy Broussard, Athens, GA (US); Joan S. Schrader, Ashland, NE (US)

(73) Assignee: Intervet Inc., Summit, NJ (US)

( * ) Notice: Subject to any disclaimer, the term of this patent is extended or adjusted under 35 U.S.C. 154(b) by 599 days.

(21) Appl. No.: 12/472,805

(22) Filed: May 27, 2009

(65) Prior Publication Data

US 2010/0015182 A1 Jan. 21, 2010

Related U.S. Application Data

(60) Provisional application No. 61/057,003, filed on May 29, 2008.

(51) Int. Cl.
| | | |
|---|---|---|
| *A61K 39/012* | (2006.01) | |
| *A61K 39/002* | (2006.01) | |
| *A61P 33/02* | (2006.01) | |
| *A61K 39/00* | (2006.01) | |

(52) U.S. Cl.
CPC ........... *A61K 39/012* (2013.01); *A61K 2039/52* (2013.01); *A61K 2039/522* (2013.01); *A61K 2039/552* (2013.01)

(58) Field of Classification Search
None
See application file for complete search history.

(56) References Cited

U.S. PATENT DOCUMENTS

| | | | |
|---|---|---|---|
| 4,301,148 | A | 11/1981 | Shibata et al. |
| 4,438,097 | A | 3/1984 | Shirley |
| 4,935,007 | A | 6/1990 | Bafundo et al. |
| 5,006,341 | A | 4/1991 | Davis et al. |
| 5,055,292 | A | 10/1991 | McDonald et al. |
| 5,882,672 | A | 3/1999 | Kojima et al. |
| 6,306,385 | B1 | 10/2001 | Lee |
| 6,432,646 | B1 | 8/2002 | Gasser et al. |
| 6,495,146 | B1 | 12/2002 | Evans et al. |
| 6,500,438 | B2 | 12/2002 | Evans et al. |
| 6,908,620 | B2 | 6/2005 | McDougald et al. |
| 6,969,602 | B1 | 11/2005 | Danforth et al. |
| 6,998,126 | B2 | 2/2006 | Davelaar |
| 6,998,127 | B2 | 2/2006 | McDougald et al. |
| 7,018,640 | B2 | 3/2006 | Evans et al. |
| 7,166,290 | B2 | 1/2007 | Hutchins et al. |
| 7,211,265 | B2 | 5/2007 | Richards et al. |
| 7,247,309 | B2 | 7/2007 | Vermeulen et al. |
| 7,250,286 | B2 | 7/2007 | Ellison |
| 7,354,593 | B2 | 4/2008 | McDougald et al. |
| 2001/0005910 | A1 | 6/2001 | Vermeulen et al. |
| 2002/0009765 | A1 | 1/2002 | Lee et al. |
| 2002/0160022 | A1 | 10/2002 | Schasteen et al. |
| 2004/0120973 | A1 | 6/2004 | McDougald et al. |
| 2004/0175391 | A1 | 9/2004 | Schasteen et al. |
| 2005/0244437 | A1 | 11/2005 | Van Poppel et al. |
| 2006/0165731 | A1 | 7/2006 | McDonald et al. |
| 2007/0026023 | A1 | 2/2007 | McDougald et al. |
| 2008/0031896 | A1 | 2/2008 | Vermeulen et al. |
| 2008/0131463 | A1 | 6/2008 | Stewart-Brown et al. |
| 2010/0166803 | A1 | 7/2010 | Fitz-Coy et al. |

FOREIGN PATENT DOCUMENTS

| | | |
|---|---|---|
| EP | 0047662 | 3/1982 |
| EP | 0134703 | 3/1985 |
| EP | 0256878 | 2/1988 |
| EP | 0258045 | 3/1988 |
| EP | 0294941 | 12/1988 |
| EP | 0506211 | 9/1992 |
| EP | 0761103 | 3/1997 |
| EP | 0831896 | 4/1998 |
| EP | 0831897 | 4/1998 |
| EP | 1476558 | 11/2004 |
| EP | 1569687 | 9/2005 |
| WO | WO 85/00752 | 2/1985 |
| WO | WO 88/08699 | 11/1988 |
| WO | WO 95/34218 | 12/1995 |
| WO | WO 96/40233 | 12/1996 |
| WO | WO 96/40234 | 12/1996 |
| WO | WO 99/08704 | 2/1999 |
| WO | WO 99/50387 | 10/1999 |
| WO | WO 99/66953 | 12/1999 |
| WO | WO 01/68909 | 9/2001 |
| WO | WO 02/37961 | 5/2002 |
| WO | WO 03/020917 | 3/2003 |
| WO | WO 03/072044 | 9/2003 |
| WO | WO 2004/026903 | 4/2004 |
| WO | WO 2004/052393 | 6/2004 |
| WO | WO 2005/089262 | 9/2005 |
| WO | WO 2006/113594 | 10/2006 |
| WO | WO 2010/056709 | 5/2010 |

OTHER PUBLICATIONS

Thompson et al, "Clustal W: Improving the Sensitivity of Progressive Multiple Sequence Alignment Through Sequence Weighting, Position-Specific Gap Penalties and Weight Matrix Choice", Nucleic Acid Research, vol. 22, pp. 4673-4680 (1994).

(Continued)

*Primary Examiner* — Robert A Zeman

(57) ABSTRACT

The present invention discloses a vaccine that provides protection from coccidiosis, and methods of making and using the vaccine alone, or in combination with other protective agents.

22 Claims, No Drawings

(56) References Cited

OTHER PUBLICATIONS

Vermeulen, "Progress in Recombinant Vaccine Development Against Coccidiosis: A Review and Prospects into the Next Millennium", International Journal for Parasitology, vol. 28, pp. 1121-1130 (1998).

Woods et al, "High-Resolution Electrophoretic Procedures for the Identification of Five *Eimeria* Species from Chickens, and Detection of Population Variation", Electrophoresis, vol. 21, pp. 3558-3563 (2000).

Shirley, et al., "The Biology of Avian *Eimeria* with an Emphasis on their Control by Vaccination", Advances in Parasitology, vol. 60, pp. 285-330 (2005).

Williams, "Epidemiological Aspects of the Use of Live Anticoccidial Vaccines for Chickens", International Journal for Parasitology, vol. 28, No. 7, pp. 1089-1098 (1998).

Schrader, et al., "Oocyst Cycling and Shedding Pattern of a Novel Coccidiosis Vaccine" Poster 30, AAAP Conference, 2010, Atlanta, GA, Intervet Schering-Plough Animal Health.

Schrader, et al., "Efficacy of a Novel Coccidiosis Vaccine Containing Both Precocious and Non-Precocious *Eimeria* Strains Against Virulent *E. maxima* Challenge" Poster 31, AAAP Conference, 2010, Atlanta, GA, Intervet Schering-Plough Animal Health.

International Search Report for corresponding PCT/US2009/045241, mailed Nov. 23, 2009.

Cozma, "Updates in the Immunoprophylaxis of *Eimeria* in Animals", Bul. Un. Agric. Zoo Med. Vet., 1993, pp. 185-190, vol. 47, Database Accession No. 19942203769 (Translation Attached).

Bedrnik et al., "Field Vaccination of Broilers Against Coccidiosis", Avian Pathology, 1989, pp. 255-264, vol. 18.

Long et al., "*Eimeria*: Further Studies on the immunisation of Young Chickens Kept in Litter Pens", Avian Pathology, 1979, pp. 213-228, vol. 8.

Long et al., "Immunisation Against Coccidiosis in Chickens: Tests Under Simulated Field Conditions", Avian Pathology, 1982, pp. 131-144, vol. 11.

Suo et al., "The efficacy and economic benefits of Supercox, a live anticoccidial vaccine in a commercial trial in broiler chickens in China", Veterinary Parasitology, 2006, pp. 63-70, vol. 142.

Xun et al., "Field trial of Supercox, a live coccidiosis vaccine, in broilers", Chinese Journal of Veterinary Medicine, 2003, pp. 9-12, vol. 39, No. 9 (Translation Attached).

COCCIDIOSIS VACCINES

CROSS-REFERENCE TO RELATED APPLICATIONS

This application is a non-provisional application that claims priority under 35 U.S.C. §119(e) of provisional application U.S. Ser. No. 61/057,003 filed May 29, 2008, the content of which is hereby incorporated by reference in its entirety.

FIELD OF THE INVENTION

The present invention relates to vaccines that provide protection from coccidiosis. Methods of making and using the vaccines alone, or in combination with other protective agents, are also provided.

BACKGROUND

Coccidiosis is an enteric disease of animals that afflicts domestic livestock worldwide. Businesses that rely on animal production often face significant costs because of coccidiosis, including financial losses due to the diseased livestock, as well as the expenses for the prophylactic treatments intended to reduce and/or prevent the disease. Such costs are especially relevant to the poultry industry, where intensive housing of birds favors the spread of coccidiosis.

The etiological causes of coccidiosis are members of the obligate intracellular sporozoa, subclass, *Coccidia*. One genus of this subclass that has significant impact on animal production is *Eimeria*. As is true for closely related genera *Isospora*, *Cystoisospora*, and *Cryptosporidium*, *Eimeria* requires only a single host to complete its life cycle. Under natural conditions, this life cycle begins with the ingestion of sporulated oocysts from the environment.

*Eimeria* are single-celled parasites with a complex, monoxenous life cycle, that exhibit a high degree of both host-species and tissue specificity. *Eimeria* species include those that are found in chickens: *E. tenella, E. acervulina, E. maxima, E. necatrix, E. mitis, E. praecox, E. mivati* and *E. brunetti*; and those found in turkeys: *E. meleagrimitis, E. adenoeides, E. gallopavonis, E. dispersa, E. meleagridis, E. innocua*, and *E. subrotunda*. The stages of the life cycle of *Eimeria* are essentially the same for all species of *Eimeria*, although each species has a preferred site in the intestine for development and the time required to complete the life cycle varies from species to species.

Numerous *Eimeria* species can infect a single host via the oral route, nasal route and/or by entry of the infectious particles into the lacrimal duct. Once ingested, the parasites penetrate the intestinal mucosal cells and undergo asexual and sexual stages of the life cycle. The resulting intestinal damage can ultimately lead to impaired growth (stunting), decreased feed utilization, loss of pigmentation, and increased mortality. In addition, the damage to the intestinal lining predisposes the animal to other infectious conditions, e.g., afflicted chickens become more prone to *Clostridium perfringens*-induced necrotic enteritis.

Infection begins with ingestion by a host of sporulated *Eimeria* oocysts. The ingested oocysts then release sporocysts in the intestine of the host. The sporocysts release sporozoites that enter intestinal epithelial cells and then transform into trophozoites. The trophozoites, in turn, undergo a process known as merogony to form first generation schizonts. Due to their relatively large size, it is the schizonts that cause the principal pathogenic effect of the infection, i.e., the tissue damage to the host.

Early generation schizonts produce numerous merozoites, which are released, and then grow and form the next-generation of schizonts. This asexual phase continues for a variable number of generations prior to the beginning of the sexual phase. The sexual phase starts when the schizonts form microgametocytes and macrogametes. The microgametocytes subsequently develop into microgametes that fertilize the macrogametes to produce unsporulated oocyst progeny. The unsporulated oocysts are then released into the intestinal lumen and excreted with the host feces. The completion of the life cycle, heralded by emergence of unsporulated oocysts in the host feces, is known as patency.

Sporulation of the oocysts occurs outside of the host, when the environmental conditions are favorable. The inevitable ingestion by a host of the sporulated oocysts begins the next cycle of infection. The time from host ingestion of the sporulated oocysts to emergence of the unsporulated oocysts in the feces is termed the prepatent time period. The prepatent time period differs among the various *Eimeria* species.

Poultry that are repeatedly exposed to *Eimeria* infections can acquire immunity from coccidiosis. In fact, depending on the immunogenicity of each *Eimeria* species, daily infection of broilers with small numbers of sporulated oocysts can result in the birds acquiring full immunity after as little as two repeated infections. Consequently, current protocols employing live *Eimeria* vaccines are based on the principle of acquired immunity, i.e., repeated infections with a small number of infective oocysts.

Vaccination generally is performed in the hatchery on the day of the bird's birth by administering the live *Eimeria* vaccine directly onto the birds, or through its application over their feed and/or drinking water. The infective oocysts complete their life cycle inside the intestinal tract of the bird, as described above, culminating with the release of a new generation of unsporulated oocysts in 5-11 days, depending on the species of the *Eimeria*. The unsporulated oocysts excreted with the feces then become infective, i.e., sporulate, in the outside environment, and re-infect the birds through host ingestion. Following two or three such cycles, the birds become immunized against coccidiosis. This immunity is characterized by: (i) a decrease and/or absence of parasites observed microscopically in the intestine, (ii) a reduction of the shedding of the oocysts, (iii) a reduction of the intestinal lesions, (iv) a reduction of the clinical disease, and/or (v) a reduction or prevention of weight lost. The acquired immunity wanes over a three to four month time period in the absence of subsequent exposure to infective oocysts.

Wild-type *Eimeria* are generally isolated from outbreaks of clinical disease in poultry flocks and may be propagated for use as pathogenic challenge strains. Typical non-attenuated vaccines are composed of infective oocysts from mildly to moderately pathogenic strains of the different *Eimeria* species that have been maintained by laboratory passage. These non-attenuated *Eimeria* are capable of causing coccidiosis when ingested in high numbers. Vaccine makers and users have to be careful to ensure that the vaccination provides just enough infective oocysts to elicit immunity, but not disease in the naive host. After the initial dose, the vaccination process relies solely on re-infection through the host's ingestion of sporulated oocysts from the litter.

Attenuated vaccines are made up of infective oocysts that have reduced pathogenicity. Due to the strong correlation between attenuated pathogenicity and possession of a shorter prepatent period, many attenuated strains are also precocious.

Consistently, attenuated lines that possess shortened prepatent periods are commonly termed "precocious lines".

Accordingly, some attenuation of the pathogenicity of *Eimeria* can be achieved through selecting for the early appearance of oocysts during repeated passage of the parasites in the host animal. In this way, populations of a given species of *Eimeria* have been identified that have greatly reduced prepatent time periods, and greatly reduced pathogenicity. Although the cause of the observed reduced pathogenicity is not completely understood, it is generally believed to be linked with the depletion and/or reduction in the size of at least one generation of schizonts, thereby reducing the tissue damage in the host.

There are advantages and disadvantages for both non-attenuated and attenuated vaccines. One advantage to vaccines made up of non-attenuated parasites is that the parasites replicate in larger numbers resulting in faster accumulation of oocysts in the environment, which is necessary for re-infection and subsequent immunization of the birds. On the other hand, the process of replication of non-attenuated *Eimeiria* in the intestinal tract of a naive chicken can produce lesions that result in poor animal welfare, loss of feed efficiency, and other detrimental effects, including secondary infections and inflammation.

Another disadvantage of non-attenuated vaccines is the necessity of ensuring that each bird receives the correct initial dose, since too large of an inoculum will cause heavy intestinal lesions, and too small an inoculum will result in a delay in onset of the immunization process, relative to the flock. In the latter case, the birds that receive an insufficient initial dose can become susceptible to being overwhelmed by the challenge due to the amplified number of infective oocysts excreted by their flock mates subsequent to the initial prepatent period. Indeed, lack of sufficient immunity prior to such subsequent *Eimeria* challenge(s) probably accounts for most of the failures experienced when a live non-attenuated vaccine is used.

One major advantage of attenuated vaccines is that they cause only minimal lesions. Attenuated vaccines, however, produce fewer oocysts than non-attenuated strains, resulting in slower accumulation of infective oocysts in the environment thereby, lowering the probability of re-infection following the initial prepatent period. This, in turn, results in a longer time required for the immunization to become fully established, and can even interrupt the overall immunization process. The slower accumulation of infective oocysts in the environment is particularly problematic when immunizing against the *Eimeria* species, *E. maxima*, because wild-type *E. maxima* produce relatively large numbers of oocysts.

Since a single host species can be infected by multiple *Eimeria* species, live vaccines against coccidiosis are usually designed to comprise oocysts from a number of *Eimeria* species. Heretofore, there have been only three types of such live vaccines: non-attenuated vaccines consisting of only laboratory cultivated oocysts; attenuated vaccines consisting of only attenuated oocysts; and mixed vaccines in which the oocysts from some *Eimeria* species are non-attenuated, and the oocysts from other *Eimeria* species are attenuated. Unfortunately, none of these vaccines overcome the disadvantages noted above. Indeed, in view of the significant disadvantages of each of the current types of live *Eimeiria* vaccines, along with the considerable cost to the industry of the coccidiosis due to *Eimeria* infections, there remains a longstanding need for improved vaccines that can better protect poultry from this costly enteric disease.

The citation of any reference herein should not be construed as an admission that such reference is available as "prior art" to the instant application.

SUMMARY OF THE INVENTION

Accordingly, the present invention provides new immunogenic compositions that may be used in vaccines against coccidiosis. In one aspect of the present invention, a vaccine is provided that comprises at least two different strains of a single species of a sporozoan *Coccidia* genus, and that at least two different strains of the single species of the sporozoan *Coccidia* genus possess an asynchronous prepatent period relative to each other.

In one embodiment, the vaccine composition comprises a first strain of a species of a genus of *Coccidia* along with a second strain of that same species in which the first strain and the second strain possess an asynchronous prepatent period. In one such embodiment, the *Coccidia* genus is *Isospora*. In another embodiment, the *Coccidia* genus is *Cystoisospora*. In still another embodiment, the *Coccidia* genus is *Cryptosporidium*. In a particular embodiment, the *Coccidia* genus is *Eimeria*.

Multivalent vaccines are also provided that comprise any and all combinations of *Coccidia* genuses. In particular embodiments, vaccines are provided that comprise two or more strains of two or more of such individual *Coccidia* genuses. In an embodiment of this type, the vaccine comprises pairs of strains of multiple *Coccidia* genuses in which multiple pairs of strains of single species of the *Coccidia* genus(es) possess asynchronous prepatent periods. In a particular embodiment the vaccine comprises pairs of strains of a single species of *Cystoisospora* that possess an asynchronous prepatent period and pairs of strains of a single species of *Isospora* that possess an asynchronous prepatent period. In another embodiment all of the pairs of strains of single species of the *Coccidia* genus(es) in the vaccine possess asynchronous prepatent periods.

In one embodiment, the first strain of the species of the sporozoan, *Coccidia* genus in the vaccine is a non-attenuated strain and the second strain is a precocious strain. In a particular embodiment of this type, the precocious strain is also an attenuated strain.

The vaccines of the present invention can comprise sporozoans at any stage in their life-cycle including mixtures of one or more, or even all stages of their life-cycles. In a particular embodiment, the sporozoans in the vaccine are oocysts. In another embodiment the sporozoans are sporozoites. In still another embodiment the sporozoans are merozoites. In yet another embodiment, the sporozoans are a mixture of merozoites and/or sporozoites and/or oocysts.

In one aspect of the present invention vaccines are provided that comprise non-attenuated sporozoans and precocious sporozoans of the same species of a genus of *Coccidia* that are in defined ratios and/or quantities. Thus, in a particular embodiment, a vaccine of the present invention comprises non-attenuated sporozoans and precocious sporozoans of the same species of a genus of *Coccidia* in which the ratio of non-attenuated sporozoans to precocious sporozoans in the vaccine is about 1 non-attenuated sporozoan to about 4 precocious sporozoans. In another embodiment of this type, the ratio of non-attenuated sporozoans to precocious sporozoans of the same species is about 1 non-attenuated sporozoan to about 2 precocious sporozoans. In still another embodiment the ratio of non-attenuated sporozoans to precocious sporozoans of the same species is about 1 non-attenuated sporozoan to about 1 precocious sporozoan. In yet another embodiment the ratio of non-attenuated sporozoans to precocious sporozoans of the same species is about 2 non-attenuated sporozoans to about 1 precocious sporozoan. In still another embodiment the ratio of non-attenuated sporozoans to precocious sporozoans of the same species is about 4 non-attenuated sporozoans to about 1 precocious sporozoan. In specific embodiments of this type the non-attenuated sporozoans are non-attenuated oocysts. In another embodiment the precocious sporozoans are precocious oocysts. In still another vaccine embodiment, the non-attenuated sporozoans are non-attenuated oocysts, and the precocious sporozoans are precocious oocysts.

Vaccines are also provided, which comprise any and/or all combinations and quantities of strains of the same species of a genus of *Coccidia*, which have asynchronous prepatent periods. In a particular embodiment of this type, the vaccine comprises about 10 to about 1000 non-attenuated oocysts. In another embodiment the vaccine comprises about 25 to about 500 non-attenuated oocysts. In still another embodiment the vaccine comprises about 50 to about 250 non-attenuated oocysts. In yet another embodiment the vaccine comprises about 100 to about 200 non-attenuated oocysts.

In a related embodiment of this type, the vaccine comprises about 50 to about 20000 non-attenuated oocysts. In another embodiment the vaccine comprises about 100 to about 10,000 non-attenuated oocysts. In still another embodiment the vaccine comprises about 250 to about 5000 non-attenuated oocysts. In yet another embodiment the vaccine comprises about 500 to about 3000 non-attenuated oocysts. In still another embodiment the vaccine comprises about 750 to about 2000 non-attenuated oocysts.

In another embodiment, the vaccine comprises about 50 to about 20000 precocious and/or attenuated oocysts. In another embodiment the vaccine comprises about 100 to about 10,000 precocious oocysts. In still another embodiment the vaccine comprises about 250 to about 5000 precocious oocysts. In yet another embodiment the vaccine comprises about 500 to about 3000 precocious oocysts. In still another embodiment the vaccine comprises about 750 to about 2000 precocious oocysts. In still another embodiment, a vaccine of the present invention comprises about 10 to about 1000 precocious oocysts. In another embodiment the vaccine comprises about 25 to about 500 precocious oocysts. In still another embodiment the vaccine comprises about 50 to about 250 non-attenuated precocious oocysts. In yet another embodiment the vaccine comprises about 100 to about 200 precocious oocysts. In particular embodiments the precocious oocysts are attenuated oocysts.

When a vaccine of the present invention includes a particular sporozoan *Coccidia* genus, e.g., *Eimeria*, any such species can be employed. In one such embodiment the vaccine comprises an *Eimeria* species that can help protect chickens from coccidiosis. In one such embodiment the *Eimeria* species is *E. tenella*. In another embodiment the *Eimeria* species is *E. acervulina*. In yet another embodiment the *Eimeria* species is *E. necatrix*. In still another embodiment the *Eimeria* species is *E. mivati*. In yet another embodiment the *Eimeria* species is *E. mitis*. In still another embodiment the *Eimeria* species is *E. praecox*. In yet another embodiment the *Eimeria* species *E. brunette*. In a particular embodiment the *Eimeria* species is *E. maxima*.

Vaccines are also provided that comprise any and all combinations of such *Eimeria* species. In addition, vaccines are provided that comprise two or more strains of two or more of such individual species. In one embodiment of this type, the vaccine comprises pairs of strains of multiple *Eimeria* species in which multiple pairs of strains of single *Eimeria* species possess asynchronous prepatent periods. In a particular embodiment of this type, all of the pairs of strains of single *Eimeria* species in the vaccine possess asynchronous prepatent periods.

In a specific embodiment, a vaccine comprises a wild type and/or non-attenuated strain of *E. maxima* and an attenuated and/or precocious strain of *E. maxima*. In one such embodiment the wild type and/or non-attenuated strain of *E. maxima* have essentially all the identifying characteristics and/or essentially all of the properties of the *E. maxima* strain found in the vaccine sold under the name COCCIVAC®. In another specific embodiment of this type a vaccine comprises an attenuated and/or precocious strain of *E. maxima* that has essentially all the identifying characteristics and/or essentially all of the properties of the *E. maxima* strain found in the vaccine sold under the name PARACOX®. In still another embodiment, a vaccine comprises a wild type and/or non-attenuated strain of *E. maxima* having essentially all the identifying characteristics and/or essentially all of the properties of the *E. maxima* strain found in the vaccine sold under the name COCCIVAC® and an attenuated, precocious strain of *E. maxima* that has essentially all the identifying characteristics and/or essentially all of the properties of the *E. maxima* strain found in the vaccine sold under the name PARACOX®.

Another vaccine of the present invention comprises one or more *Eimeria* species that can help protect turkeys from coccidiosis. In one such embodiment the *Eimeria* species is *E. meleagrimitis*. In another embodiment the *Eimeria* species is *E. adenoeides*. In still another embodiment the *Eimeria* species is *E. gallopavonis*. In yet another embodiment the *Eimeria* species is *E. dispersa*. In still another embodiment the *Eimeria* species is *E. meleagridis*. In yet another embodiment the *Eimeria* species is *E. innocua*. In still another embodiment the *Eimeria* species is *E. subrotunda*. Vaccines are also provided that comprise any and all combinations of turkey *Eimeria* species. In addition, vaccines are provided that comprise two or more strains of two or more of such individual species. In one embodiment of this type, the vaccine comprises pairs of strains of multiple turkey *Eimeria* species in which multiple pairs of strains of single turkey *Eimeria* species possess asynchronous prepatent periods. In a particular embodiment of this type, all of the pairs of strains of single turkey *Eimeria* species in the vaccine possess asynchronous prepatent periods.

In another aspect of the present invention vaccines are provided that include one or more species and/or strains of species of *Isospora, Cystoisospora*, and/or *Cryptosporidium*. In such embodiments of this type, at least two strains of the species of *Isospora, Cystoisospora*, and/or *Cryptosporidium* also possess an asynchronous prepatent period. In addition, any of the *Eimeria* vaccines of the present invention can be combined with such *Isospora, Cystoisospora*, and/or *Cryptosporidium* vaccines.

In a particular embodiment, a vaccine includes a non-attenuated strain of a species of *Cryptosporidium* and a precocious strain of the same species of *Cryptosporidium*. In another embodiment such a *Cryptosporidium* vaccine further comprises a non-attenuated strain of a species of *Isospora* and a precocious strain of the same species of *Isospora*. In still another embodiment the *Cryptosporidium* vaccine further comprises a non-attenuated strain of a species of *Cystoisospora* and a precocious strain of the same species of *Cystoisospora*. In yet another embodiment the *Cryptosporidium* vaccine further comprises a non-attenuated strain of a species of *Cystoisospora*, a precocious strain of the same species of

*Cystoisospora*, a non-attenuated strain of a species of *Isospora*, and a precocious strain of the same species of *Isospora*.

In related embodiment the present invention provides a vaccine that includes a non-attenuated strain of a species of *Isospora* and a precocious strain of the same species of *Isospora*. In another embodiment the vaccine includes a non-attenuated strain of a species of *Cystoisospora* and a precocious strain of the same species of *Cystoisospora*. In still another embodiment the vaccine comprises a non-attenuated strain of a species of *Cystoisospora*, a precocious strain of the same species of *Cystoisospora*, a non-attenuated strain of a species of *Isospora*, and a precocious strain of the same species of *Isospora*.

In another aspect of the invention, methods of immunizing an animal subject against coccidiosis are provided. One such embodiment comprises administering to the animal an immunologically effective amount of any vaccine of present invention. In one embodiment the vaccine is administered orally. In another embodiment the vaccine is administered in ovo. In still another embodiment the vaccine is administered topically. In yet another embodiment the vaccine is administered by injection.

In one particular embodiment the vaccine is administered in the drinking water of the animal. In another embodiment, the vaccine is administered in the food of the animal. In still another embodiment the vaccine is both administered in the food and the drinking water of the animal.

In yet another embodiment the vaccine is administered by spraying. In one such embodiment, a solution containing the vaccine is sprayed over day-old chicks. In a specific embodiment of this type the day-old chicks are vaccinated using a spray cabinet in their hatchery. In still another embodiment the vaccine is administered by applying the vaccine to the eye of the animal. In a specific embodiment of this type the application of the vaccine to the eye of the animal is performed with an eye-dropper. In still another embodiment the vaccine is administered by two, three, four, or more means of administration.

In a particular embodiment, a vaccine of the present invention is administered to an avian. In one embodiment the avian is a domesticated bird. In one such embodiment, the animal is a chicken. In another embodiment the domesticated bird is a turkey. In yet another embodiment the domesticated bird is a duck. In still another embodiment the domesticated bird is a game bird. In a particular embodiment of this type the game bird is a quail. In another embodiment the game bird is a pheasant. In still another embodiment the vaccine is administered to a mammal. In a particular embodiment of this type, the mammal is a non-human mammal.

These and other aspects of the present invention will be better appreciated by reference to the Detailed Description and Example.

DETAILED DESCRIPTION OF THE INVENTION

The present invention, therefore, provides a vaccine against coccidiosis formulated to maximize the advantages of distinct properties of non-attenuated and precocious *Coccidia* vaccines respectively, while minimizing their individual drawbacks. In one aspect of the invention, a vaccine comprises a combination of one or more strains of a wild-type *Coccidia* species with one or more strains of attenuated *Coccidia* from the same species. Such a vaccine can engender a stronger immune response from the host than that for the two individual types of strains alone. Moreover, the resulting dual and disparate parasitic life-cycles of these two types of strains can expedite the attainment of solid immunity in the host.

In general, it takes longer to attain solid immunity against a given species of *Eimeria* with a vaccine comprising a precocious strain than one employing a non-attenuated strain, despite the fact that patency comes earlier with precocious vaccines. This result suggests that the additional replicative cycles that non-attenuated strains undergo in the prepatent period may accelerate the host's immune response relative to that observed for precocious strains, and/or that the substantially greater number of oocysts released at patency following infection/vaccination with non-attenuated *Eimeria* may bring the host animal to full immunity in fewer parasitic life-cycles.

Although in no way constrained by any particular mechanism of action, the present invention is consistent with there being a synergistic effect on the host immune system that arises through the vaccination of a host animal with a vaccine that comprises two or more strains of a chosen species of a *Coccidia* genus, e.g., of *Eimeria*, in which at least two of the strains have an asynchronous prepatent period. Such an asynchronous prepatent period allows the immunization process to proceed faster than that found when employing either strain alone due to the reinforcing effect of the alternating patencies. Indeed, the faster succession of patencies facilitates the re-immunization process by increasing the frequency of the availability of freshly generated oocysts for the host to ingest. The reinforcing effect, termed herein as an "echo effect", can thereby elicit earlier immunity for that host animal.

Therefore, in one aspect, the present invention provides a vaccine that comprises an attenuated strain that has a shorter prepatent period, along with an non-attenuated strain of the same species that has a longer prepatent period, but much greater capacity to replicate and contaminate the environment with a new generation of oocysts. One such exemplary vaccine of the present invention includes two distinct strains (or lines) of *Eimeria maxima*: an attenuated, precocious strain derived from the same master seed used to produce the vaccine sold under the name, PARACOX®, and an unattenuated strain, derived from the master seed used to produce the vaccine sold under the name, COCCIVAC®. Both of these strains provide efficacy against an *E. maxima* field challenge. However, vaccination with an unattenuated strain results in a flock of broilers showing full immunity by the end of 3 weeks, whereas vaccination with precocious and/or attenuated vaccines takes at least four weeks to become fully established.

Due to the differing lengths of their prepatent periods, earlier immunity for the host animal can be obtained through the echo effect. Thus, by creating an asynchronous stimulation of the immune response, i.e., an echo effect, the combined *Eimeria maxima* strains can stimulate a more prolonged exposure of antigen to the immune system and thereby, accelerate the process of developing protective immunity.

Indeed, administering the two strains together can create an increase in efficiency of the immunization process. Both the non-attenuated and precocious oocysts simultaneously commence their respective life-cycles in the host, but the non-attenuated strain completes its prepatent period between 11 to 31 hours after that of the precocious strain. The non-attenuated strain also sheds a significantly larger number of oocysts into the feces.

Thus, the precocious strain completes its life cycle in the host first, thereby initiating the host's immune response. The precocious oocysts are then excreted, sporulate, and following their ingestion by the host, begin their second life-cycle. At the same time, the first life-cycle of the non-attenuated strain continues to produce one or more extra generation(s) of schizonts, ultimately resulting in the formation of gametocytes, reinforcing and expanding the immune response initiated by the precocious strain. The excreted non-attenuated oocysts then sporulate in the litter, and are ingested by a host that is already harboring the precocious strain undergoing its second life-cycle. These simultaneous asynchronous life-cycles thus serve to decrease the time required to achieve solid immunity in the host. The overall process also can allow the vaccines to contain fewer non-attenuated oocysts in the initial dose, resulting in a lowering of the number and/or a lessening of the severity of the lesions formed in the host intestine due to the non-attenuated strain infection.

The use of singular terms for convenience in description is in no way intended to be so limiting. Thus, for example, reference to a composition comprising "a quantity" includes reference to one or more of such quantities. In addition, reference to an "oocyst" includes reference to a plurality of such oocyts, unless otherwise indicated.

As used herein the following terms shall have the definitions set out below:

The terms "adjuvant" and "immune stimulant" are used interchangeably herein, and are defined as one or more substances that cause stimulation of the immune system. Adjuvants are agents that nonspecifically increase an immune response to a particular antigen, thus reducing the quantity of antigen necessary in any given vaccine, and/or the frequency of injection necessary in order to generate an adequate immune response to the antigen of interest. In this context, an adjuvant is used to enhance an immune response to one or more vaccine antigens/isolates. An adjuvant may be administered to the target animal before, in combination with, or after the administration of the vaccine.

As used herein the term "approximately" is used interchangeably with the term "about" and signifies that a value is within fifty percent of the indicated value i.e., a composition containing "approximately" 100 oocysts contains from 50 to 150 oocysts.

As used herein, an "attenuated" strain of a species of a *Coccidia* genus (such as an "attenuated *Eimeria*") is a strain that has been selected for its reduced pathogenicity in the host. Such attenuation can be achieved by a number of means including serial passage (such as serial embryo passage), chemical mutagenesis, and by irradiation methods.

As used herein, a "precocious" strain of a species of a *Coccidia* genus (such as a "precocious *Eimeria*") is a strain that has a shortened prepatent period relative to the non-attenuated strain of the same species. A precocious strain can also be an attenuated strain.

As used herein, a "wild-type" strain of a species of a *Coccidia* genus (such as a "wild-type *Eimeria*") is a field isolate which has not been altered by attenuating passage or any other treatment including selection by: single oocyst isolation, immune tolerance, or other segregative process.

As used herein, a "non-attenuated" strain of a species of a *Coccidia* genus (such as "non-attenuated *Eimeria*") is a strain that neither has a shortened prepatent period nor reduced pathogenicity in the host relative to the wild-type strain of the same species.

As used herein, a "strain" of a species of a *Coccidia* genus (e.g., a species of *Eimeria*) is a subpopulation of the species of the *Coccidia* genus that can be differentiated from the general population of that species by one or more of the following features: pathogenicity, immunogenicity, prepatent period, and/or a population resulting from expansion of a single oocyst.

The term "asynchronous prepatent time period" refers to prepatent time periods of two or more species of a *Coccidia* genus and/or two or more strains of a species of a *Coccidia* genus that differ by 10% or greater. In a particular embodiment, two or more species of a *Coccidia* genus and/or two or more strains of a single species of a *Coccidia* genus have asynchronous prepatent periods that differ by 20% or greater. In still another embodiment, two or more species of a *Coccidia* genus and/or two or more strains of a single species of a *Coccidia* genus have asynchronous prepatent periods that differ by 25% or greater.

In reference to asynchronous prepatent periods for precocious and/or attenuated strains with nonattenuated strains that differ by a percentage (%) of time, the percentage is based on the non-attenuated strain's prepatent time period. Thus, when a non-attenuated strain of a *Coccidia* genus has a prepatent period of 120 hours and a precocious strain of the same species of the *Coccidia* genus has a prepatent period of 108 hours, the two strains have asynchronous prepatent periods that differ by 10%.

The term "domesticated bird(s)", as used herein, unless otherwise indicated, includes chickens, turkeys, ducks, game birds (including, but not limited to, quail, pheasants, and geese) and ratites (including, but not limited to emu and ostriches).

The term "*Eimeria*", as used herein, unless otherwise indicated, means one or more species of the genus *Eimeria* that infect domesticated birds. *Eimeria* species include those that are found in chickens, and include, e.g., *E. tenella, E. acervulina, E. maxima, E. necatrix, E. mitis, E. praecox, E. mivati* and *E. brunette*, and also those that are found in turkeys, including *E. meleagrimitis, E. adenoeides, E. gallopavonis, E. dispersa, E. meleagridis, E. innocua*, and *E. subrotunda*, and also *Eimeria* species that infect other domesticated birds as defined above. The term "*Eimeria*" also includes all strains of the foregoing species of *Eimeria*, including, but not limited to, precocious strains, and attenuated strains, which also includes strains that have been irradiated, or otherwise treated, so that they fail to complete development. The term *Eimeria* further includes any newly-discovered strains or species of *Eimeria* that infect domesticated birds as defined above.

The term "encysted" means the oocyst stage of the protozoan parasite.

As used herein, the terms "immunize" and "vaccinate" are synonymous and are used interchangeably. The term "effective immunizing dose", as used herein, unless otherwise indicated, means the number of sporozoans at any stage in their life-cycle including mixtures of one or more, or even all stages of their life-cycles, e.g., sporozoites, oocysts and/or merozoites, or, when mixed, e.g., the number of sporozoites, oocysts and merozoites, sufficient to elicit an immune reaction in animals so vaccinated, e.g., elicit a rise in corresponding antibody titers and/or an activation of cell-mediated immunity. Preferably, the immune reaction that is elicited provides protective immunity that limits or reduces clinical disease signs, weight loss, morbidity, and/or mortality in the vaccinated animals (e.g., avians) when challenged with a virulent dose of the sporozoa (e.g., *Eimeria* or *Cryptosporidia*).

The terms "oocysts", "merozoites" and "sporozoites", as used herein, and unless otherwise indicated, mean viable, i.e., live, *Coccidia* (e.g. *Eimeria* or *Cryptosporidia*) oocysts, merozoites and sporozoites that can be either attenuated or non-attenuated.

The term "solid immunity" is used interchangeably herein with the term "full immunity" and denotes a degree of immunity bestowed on a group of vaccinated animals (e.g., a flock of vaccinated birds) that provides protection against an homologous challenge such that the vaccinated animals are statistically similar to non-challenged controls (and/or statistically dissimilar to non-vaccinated challenged controls) in health and performance as measured by e.g., feed conversion, weight gain, and/or lesions (gross or microscopic) of coccidiosis.

The term "statistically similar" as used herein denotes that a statistical comparison of the two groups or populations of animals would result in acceptance of the null hypothesis (or hypothesis of no difference) at a level of significance of <0.1.

The term "statistically dissimilar" as used herein denotes that a statistical comparison of the two groups or populations of animals would result in rejection of the null hypothesis (or hypothesis of no difference) at a level of significance of <0.1.

The term "sporocyst" refers to the capsule that encloses the sporozoites in the oocyst.

Animal Subjects

The animal to be so treated is preferably, but not exclusively, a vertebrate, and more preferably a mammal, avian or fish. Any of the inventive vaccines may be administered to the animal subject. Appropriate animal subjects include those in the wild, livestock (e.g., raised for meat, milk, butter, eggs, fur, leather, feathers and/or wool), beasts of burden, research animals, companion animals, as well as those raised for/in zoos, wild habitats and/or circuses.

Birds (Avians) treated or protected by the inventive vaccines can be associated with either commercial or noncommercial aviculture. These include e.g., *Anatidae*, such as swans, geese, and ducks, *Columbidae*, e.g., doves and pigeons, such as domestic pigeons, *Phasianidae*, e.g., quail, partridge, grouse, pheasants, and turkeys, *Thesienidae*, e.g., domestic chickens, *Psittacines*, e.g., parakeets, macaws, and parrots, e.g., raised for the pet or collector market, among others.

Mammalian subjects include bovine (e.g., cattle or dairy cows), porcine (e.g., hogs or pigs), ovine (e.g., goats or sheep), equine (e.g., horses), canine (e.g., dogs), feline (e.g., house cats), camels, deer, antelopes, rabbits, guinea pigs and rodents (e.g., squirrels, rats, mice, gerbils, and hamsters), *cetaceans* (whales, dolphins, porpoise), *pinnipeds* (seals, walrus).

Fish may also be the subject for the vaccines of the present invention. For purposes of the present invention, the term "fish" shall be understood to include without limitation, the *Teleosti* grouping of fish, i.e., teleosts. Both the Salmoniformes order (which includes the Salmonidae family) and the Perciformes order (which includes the Centrarchidae family) are contained within the *Teleosti* grouping. Examples of potential fish recipients include the Salmonidae family, the Serranidae family, the Sparidae family, the Cichlidae family, the Centrarchidae family, the three-Line Grunt (*Parapristipoma trilineatum*), and the Blue-Eyed Plecostomus (*Plecostomus* spp), among others. Still further examples of fish that can be treated include, but are not limited to catfish, sea bass, tuna, halibut, arctic charr, sturgeon, turbot, flounder, sole, carp, tilapia, striped bass, eel, sea bream, yellowtail, amberjack, grouper and milkfish.

Antigens

Wild type oocysts are obtainable from feces or tissue of infected animals; contaminated feed or water; soil; pen litter or bedding; or a variety of other sources. Methods for isolation of sporocysts and oocysts are known. The exact procedures used to separate oocysts will vary with the material from which the oocysts are obtained and will be readily apparent to those skilled in the art. Merozoites can be grown in culture by methods as e.g., disclosed in U.S. Pat. No. 7,250,286 B2.

One available approach to isolating organisms from raw environmental samples is as follows: The initial step is separation of the sporocysts and/or oocysts from extraneous material. Soil or excreta is generally processed by forming a slurry with saturated saline solution and separating the sporocysts and/or oocysts from the slurry. For example, the material to be processed is mixed with a minimum of 2 volumes (w/v) of saturated aqueous NaCl to form a slurry. If necessary, the slurry can be processed in a mixer or blender until a homogenous consistency is achieved. The slurry is centrifuged at about 800×g for 10 minutes at 4° C. The supernatant is collected by pouring through a double layer of 24×24 weave cheese cloth. Other methods to purify oocysts from samples that are commonly used include the Sheather sucrose flotation and Zinc-sulfate flotation, [e.g., see L R Ash and T C Orihel, *Parasites: A Guide to Laboratory Procedures and Identification*, ASCP Press© 1991.

The filtered supernatant is diluted with two volumes of potable water and centrifuged at about 160033 g for 10 minutes at 4° C. The pelleted oocysts are washed with water and pelleted by centrifugation as described an additional three times. The oocysts are then washed three times in 2.5% potassium dichromate using the same procedure used for the water washes. After the final wash, the oocysts can be stored in 2.5% potassium dichromate at 4° C. or transferred to a container for sporulation.

Alternatively, sequential filtration can be used to isolate oocysts based on size. If filtration is used, the oocysts are washed with water and 2.5% potassium dichromate as previously described.

Non-attenuated lines that originated as wild-type field isolates have been maintained in laboratory settings by serial passage over many years and are well characterized as low to moderate in pathogenicity, with moderate to high fecundity, defined prepatent periods and known patterns of shedding from the host.

Aside from existing precocious *Eimeria* lines, as exemplified in U.S. Pat. No. 5,055,292, the content of which is hereby incorporated by reference in its entirety, precocious lines also can be obtained from wild-type, virulent parent strains or non-attenuated strains following serial passage in chickens. In one such case, the oocysts are collected from the feces only during the first few hours after patency. In this manner, the prepatent time period can be progressively reduced. This type of passage is termed a selection passage. Alternatively, in order to increase the numbers of oocysts available for harvest, it may be advantageous to collect oocysts at a time between the onset of patency and the approximate prepatent time period of the parent strain. This type of passage is termed a neutral passage. Finally, in the process known as relaxed passage, virtually all of the oocysts are collected, including those produced later than the prepatent time period of the parent strain.

Vaccines

Seed Lot System

Master seeds of each non-attenuated or attenuated *Eimeria* line, for example, can be stored in liquid nitrogen. A working seed can be prepared from a sample of each master seed following inoculation into the host e.g., SPF chickens. Oocysts can be recovered from the host feces and/or caeca to generate working seeds. The working seeds are stored at 4° C. and used to initiate each vaccine production. Working seeds have a shelf life of six to 12 months after which they should be replaced. When the working seed is prepared, oocysts are only harvested up to about the prepatent time of the wild-type parent strain for that species i.e., neutral passage. When the vaccine is prepared, oocysts are harvested throughout the patent period of the infection, i.e., relaxed passage.

Rearing of Chickens

Chickens are hatched from eggs obtained from a certified SPF flock. They are maintained coccidia-free during rearing to an appropriate age for vaccine production, typically 1-12 weeks of age. The chickens are then: transferred to the vaccine production accommodation, allocated in groups to separate rooms, or transferred to isolators designated for each *Eimeria* species.

Inoculation

Each group of birds is inoculated orally with a previously determined dose of the working seed. Inoculation can be arranged according to a staggered schedule so that only one species of *Eimeria* is harvested and processed on a given working day.

Harvesting

Feces are collected, although the time and duration of collection varies from species to species. A slurry of feces (and/or caecal contents) is made in water which is then homogenised. The homogenate is washed through a 150 micron sieve and the washings are centrifuged in a continuous flow bowl centrifuge. The centrifuged deposit is resuspended in saturated salt solution and recentrifuged. The supernatant is collected, diluted with water and passed a third time through the centrifuge. The deposit is resuspended in a 2% solution of potassium dichromate.

Sporulation

The oocyst suspension in potassium dichromate solution is incubated at 29° C. for 48 hours with forced aeration to sporulate the oocysts. After sporulation the dichromate solution is removed by centrifugation and the oocysts are treated with 10% chlorox (sodium hypochlorite solution) for 10 minutes. Treated oocysts are resuspended in water and formalin is added to a concentration of 0.05%. The suspension is stored at 4° C.

Blending

Oocyst counts of each bulk oocyst solution suspension are made and calculated volumes of each suspension are mixed with a suspending agent to give a multi-component vaccine with oocysts of each species present in the desired proportions. The vaccine is filled into final containers and stored at 4° C.

Adjuvants

Some vaccine compositions of the present invention can include a pharmaceutically acceptable adjuvant. Adjuvants of the present invention may be obtained from any of a number of sources including from natural sources, recombinant sources, and/or be chemically synthesized, etc. Suitable adjuvants for the vaccination of animals include, but are not limited to, Adjuvant 65 (containing peanut oil, mannide monooleate and aluminum monostearate); Freund's complete or incomplete adjuvant; mineral gels, aluminum compounds such as aluminum hydroxide, aluminum phosphate, and alum; surfactants, such as hexadecylamine, octadecylamine, lysolecithin, dimethyldioctadecylammonium bromide, N,N-dioctadecyl-N',N'-bis (2-hydroxymethyl) propanediamine, methoxyhexadecylglycerol, and pluronic polyols; polyanions, such as pyran, dextran sulfate, poly IC, polyacrylic acid; peptides, such as muramyl dipeptide, dimethylglycine and tuftsin; and oil emulsions. Information concerning adjuvants is disclosed, e.g., in the series by *P. Tijssen* [*Practice and Theory of Enzyme Immunoassays,* 3rd Edition, Elsevier, N.Y., (1987).

Other potential adjuvants include, but are not limited to metabolizable and non-metabolizable oils, block polymers, ISCOM's (immune stimulating complexes), vitamins and minerals (including but not limited to: vitamin E, vitamin A, selenium, and vitamin B12), Quil A (saponins), polymers of acrylic acid cross-linked with polyalkenyl ethers or divinyl glycol, as sold under the trademark CARBOPOL® (e.g., CARBOPOL® 941), and a uniformly dispersed micron size oil droplets in water emulsion (e.g., as sold under the trademark Emulsigen®).

Additional examples of adjuvants, that sometimes have been referred to specifically as immune stimulants, include bacterial and fungal cell wall components (e.g., lipopolysaccarides, lipoproteins, glycoproteins, muramylpeptides, beta-1,3/1,6-glucans), various complex carbohydrates derived from plants (e.g., glycans, acemannan), various proteins and peptides derived from animals (e.g., hormones, cytokines, co-stimulatory factors), and novel nucleic acids derived from viruses and other sources (e.g., double stranded RNA, CpG). In addition, any number of combinations of the aforementioned substances may provide an adjuvant effect, and therefore, can form an adjuvant of the present invention.

A vaccine of the present invention is readily administered by any route including oral (e.g., by eyedrop, intranasal, in feed, in water, or by spray), in ovo, topically, or by injection (e.g., intravenous, subcutaneous, intramuscular, intraorbital, intraocular, intradermal, and/or intraperitoneal) vaccination. The artisan will appreciate that the vaccine composition is preferably formulated appropriately for each type of recipient animal and route of administration.

Although the vaccines of the present invention exemplify *Eimeria*, the vaccines of the present invention also can be constructed with unattenuated and attenuated and/or precocious species and/or strains of species of the closely related genera: *Isospora, Cystoisospora,* and *Cryptosporidium,* respectfully.

EXAMPLE 1

Vaccine Comprising an Attenuated and a Non-Attenuated *E. Maxima* Strain

Strains of *E. Maxima*

*Eimeria maxima* MFP: has about a 96 hour prepatent period (a reduction of up to 25 hours from the 121 hour prepatent time of the parent strain). The harvest time can between 104-110 hours, e.g., at 108-110 hours (4.5-4.58 days). Gametocytes appear at about 72 hours or earlier post-infection. The mean sizes of the schizonts and the mean numbers of merozoites therein are substantially similar to those of the parent strain.

*Eimeria maxima* Coccivac has a prepatent period of about 121 hours and production oocysts can be harvested between 144 and 192 hours.

Vaccine Formulation: Oocysts are harvested as described above and then sporulated. Product lots of sporulated oocysts of known titer are selected to provide the desired number of sporulated oocysts per volume. The preparation of the vaccine is completed by transferring suspensions of oocysts to a sterile container and then quantitatively adding to that container a 2.5% potassium dichromate solution. The vaccine is sterilely dispensed into containers, which are then sealed.

It is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting, since the scope of the present invention will be limited only by the appended claims and equivalents thereof.

What is claimed:

1. A vaccine comprising a first strain of an *Eimeria* species and a second strain of said *Eimeria* species:
   wherein the first strain and the second strain have an asynchronous prepatent period; and wherein the first strain is a non-attenuated strain and the second strain is a precocious strain.

2. The vaccine of claim 1 comprising non-attenuated *Eimeria* oocysts and precocious *Eimeria* oocysts.

3. The vaccine of claim 2 in which the quantity of non-attenuated *Eimeria* oocysts is about 10 to about 1000.

4. The vaccine of claim 2 wherein the quantity of precocious *Eimeria* oocysts is about 100 to about 10,000.

5. The vaccine of claim 4 wherein the quantity of non-attenuated *Eimeria* oocysts is about 10 to about 1000.

6. The vaccine of claim 2 that further comprises non-attenuated *Eimeria* merozoites and sporozoites, and precocious *Eimeria* merozoites and sporozoites.

7. The vaccine of claim 1 wherein said species of *Eimeria* is selected from the group consisting of *E. tenella, E. acervulina, E. maxima, E. necatrix, E. mitis, E. praecox, E. mivati* and *E. brunetti*.

8. The vaccine of claim 7 wherein said species of *Eimeria* is *E. maxima*.

9. The vaccine of claim 8 further comprising a strain of *E. tenella*, a strain of *E. acervulina*, and a strain of *E. mivati*.

10. The vaccine of claim 9 wherein the ratio of the non-attenuated strain of *E. maxima* to the precocious strain of *E. maxima* is about 2 to about 1.

11. The vaccine of claim 8 wherein the ratio of the non-attenuated strain of *E. maxima* to the precocious strain of *E. maxima* is about 2 to about 1.

12. A method of immunizing an animal subject against coccidiosis comprising administering to the animal an immunologically effective amount of the vaccine of claim 7.

13. The method of claim 12 wherein the vaccine is administered orally.

14. The method of claim 13 wherein the vaccine is administered orally by a method selected from the group consisting of adding the vaccine to the drinking water of the animal, adding the vaccine to the food of the animal, applying the vaccine to the eye of the animal, and spraying the vaccine over the animal.

15. The method of claim 12 wherein the vaccine is administered in ovo.

16. The method of claim 12 wherein the animal is a domesticated bird.

17. The method of claim 16 wherein the domesticated bird is selected from the group consisting of a chicken, a turkey, a duck, and a game bird.

18. The method of claim 17 wherein the domesticated bird is a chicken.

19. An immunogenic composition comprising a first *Eimeria* maxima strain and a second *Eimeria* maxima strain; and further comprises a strain from one or more additional species of *Eimeria* selected from the group consisting of *E. tenella, E. acervulina, E. necatrix, E. mitis, E. praecox, E. mivati* and *E. brunette*;
   wherein the first *Eimeria* maxima strain and the second *Eimeria* maxima strain have an asynchronous prepatent period; and wherein the first strain is a non-attenuated strain and the second strain is a precocious strain.

20. The immunogenic composition of claim 19 wherein said one or more additional species of *Eimeria* are *E. tenella, E. acervulina*, and *E. mivati*.

21. An immunogenic composition comprising a first strain of an *Eimeria* species and a second strain of said *Eimeria* species; wherein the first strain and the second strain have an asynchronous prepatent period; and
   wherein the first strain is a non-attenuated strain and the second strain is a precocious strain.

22. The immunogenic composition of claim 21 wherein said *Eimeria* species is selected from the group consisting of *E. meleagrimitis, E. adenoeides, E. qallopavonis, E. dispersa, E. meleaaridis, E. innocua*, and *E. subrotunda*.

* * * * *